United States Patent [19]

Hansen

[11] Patent Number: 5,144,124
[45] Date of Patent: Sep. 1, 1992

[54] GLASS CONTAINER INSPECTION MACHINE WITH PLOT DISPLAY OF CONTAINER AND LIGHT INTENSITY

[75] Inventor: Robert A. Hansen, Elmira, N.Y.

[73] Assignee: Emhart Industries, Inc., Newark, Del.

[21] Appl. No.: 615,233

[22] Filed: Nov. 19, 1990

[51] Int. Cl.⁵ .............................................. G01N 9/04
[52] U.S. Cl. .............................. 250/223 B; 356/428; 209/526
[58] Field of Search .......................... 250/223 B, 568; 356/239, 240, 428; 209/523, 526, 546; 340/674

[56] References Cited

U.S. PATENT DOCUMENTS

| | | | |
|---|---|---|---|
| 4,378,494 | 3/1983 | Miller | 250/223 B |
| 4,378,495 | 3/1983 | Miller | 356/240 |
| 4,467,350 | 8/1984 | Miller | 250/223 B |
| 4,655,349 | 4/1987 | Joseph et al. | 209/526 |
| 4,764,681 | 8/1988 | Michalski et al. | 250/563 |
| 4,902,137 | 9/1990 | Krieg et al. | 250/223 B |
| 4,931,632 | 5/1990 | Brandt | 356/240 |

Primary Examiner—David C. Nelms
Assistant Examiner—S. Allen
Attorney, Agent, or Firm—Spencer T. Smith

[57] ABSTRACT

A display generator presents a plot of rate of change of light intensity vs. number of containers and a threshold is located along this plot to separate acceptable from unacceptable containers. A rejection controller receives this threshold data and rejects containers having a higher intensity rate of change.

4 Claims, 1 Drawing Sheet

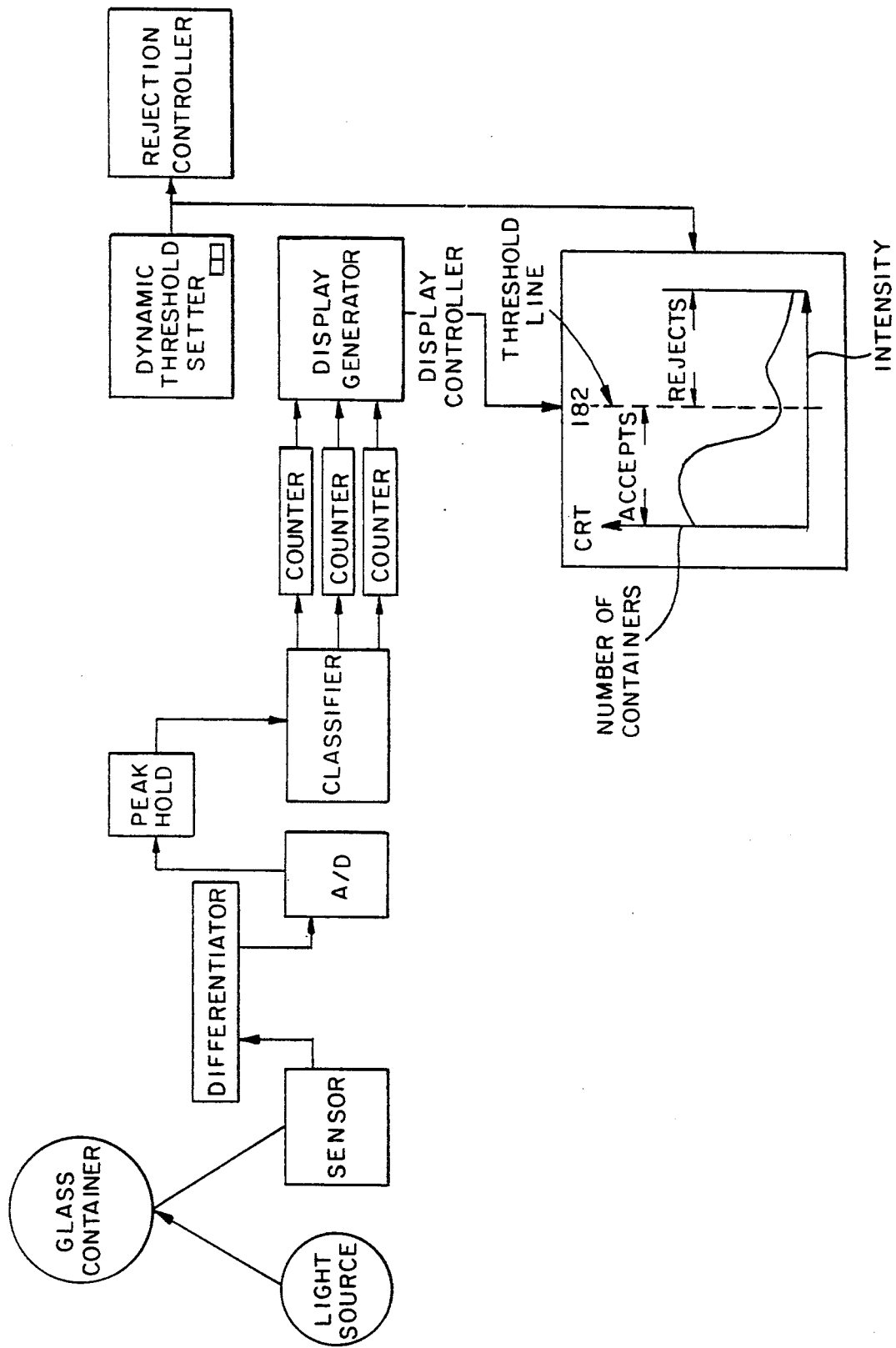

GLASS CONTAINER INSPECTION MACHINE WITH PLOT DISPLAY OF CONTAINER AND LIGHT INTENSITY

The present invention relates to machines for inspecting formed glass containers for checks.

Formed glass containers may include imperfections referred to as checks which are unacceptable. Each container is accordingly inspected to ascertain the presence of such an imperfection by illuminating the container and sensing anomalous reflections caused by such imperfections. An acceptable surface will result in a change in reflected light which is substantially less light being reflected than from a surface location having a check.

Sensors sense this reflected light and the the change in intensity of this light is converted to a digital signal representative of the rate of change of intensity. An operator selects a threshold value which will serve as the basis for the electronic controller discriminating between acceptable and unacceptable glass containers.

It is an object of the present invention to simplify the selection of this threshold value.

Other objects and advantages of the present invention will become apparent from the following portion of this specification and from the accompanying drawings which illustrate in accordance with the mandate of the patent statutes a presently preferred embodiment incorporating the principles of the invention.

Referring to the drawings:

The sole figure is a schematic presentation of an inspection machine made in accordance with the teachings of the present invention.

Formed glass containers may have unacceptable imperfections such as checks. To identify which containers are to be rejected, a Light Source directs light toward a glass container to be inspected and light reflected from the container is received by a Sensor. The derivative of the analog output of the Sensor is determined using a Differentiator. For each bottle, the peak output of the Differentiator, which is representative of the rate of change of intensity of the reflected light is converted to digital form by an A/D converter and is supplied to a Classifier which will categorize it into one of a selected number of intensity levels. Corresponding Counters will be updated for each classification and a Display Generator will present this data in the form of an X-Y plot of intensity vs. number of containers on a CRT screen or the like. Such a plot is shown on the CRT screen. As shown, acceptable containers have a lower reflection rate of change than do containers having defects such as checks and the plot gives the operator a visual picture that simplifies his task of locating the demarcation intensity separating good and bad containers. The operator can locate a threshold line at any location along the intensity axis which he believes represents the demarcation point between acceptable and unacceptable containers.

As this Threshold Line is displaced, either by depressing the jog up or jog down buttons 10, the intensity at that point along the plot is presented on the screen. When the operator finally locates this Threshold Line, the threshold value of intensity here shown to be 182 will also be finalized and the rejection controller will reject all containers having a higher rate of change of intensity value.

I claim:

1. An apparatus for inspecting formed glass containers for imperfections such as checks comprising light source means illuminating a glass container to be inspected, sensor means for sensing light reflected from the glass container to be inspected means for displaying a plot of number of containers vs. light intensity, means for selecting a predetermined light intensity along said plot for defining the demarcation between accepted formed containers and rejected formed containers, and means for rejecting formed containers having a light intensity above said predetermined light intensity.

2. An apparatus according to claim 1, wherein said displaying means comprises multiplexer means for classifying the intensity of light reflected from a plurality of inspected containers into a selected number of classifications and a corresponding plurality of counter means for counting the inspected containers in each classification.

3. An apparatus according to claim 2, wherein said displaying means further comprises display generator means for receiving the count from each of said counter means and for generating a plot of number of containers vs. intensity.

4. An apparatus according to claim 1, wherein said selecting means comprises dynamic threshold setting means for defining a threshold location along said plot and means for shifting said threshold along said plot.

* * * * *